United States Patent
Reuter et al.

(10) Patent No.: US 9,090,582 B2
(45) Date of Patent: *Jul. 28, 2015

(54) HIGHLY PURE PENTAMYCIN (71) Applicant: Biolotus Biotechnology AG, Basel (CH)

(72) Inventors: Karl Reuter, Gundelfingen (DE); Victor Meier, Gundelfingen (DE); Florian Stolz, Denzlingen (DE); Dieter Krimmer, Unteraegeri (CH); Cees Winninps, Fluh (CH)

(73) Assignee: Biolotus Biotechnology AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/947,583

(22) Filed: Jul. 22, 2013

(65) Prior Publication Data

US 2014/0094602 A1 Apr. 3, 2014

Related U.S. Application Data (62) Division of application No. 12/934,669, filed as application No. PCT/EP2009/002054 on Mar. 20, 2009, now Pat. No. 8,519,162.

(30) Foreign Application Priority Data

Apr. 1, 2008 (EP) .................................... 08006703

(51) Int. Cl.
*C07D 313/04* (2006.01)
*C07D 313/00* (2006.01)
*C07H 17/08* (2006.01)

(52) U.S. Cl.
CPC .............. *C07D 313/00* (2013.01); *C07H 17/08* (2013.01)

(58) Field of Classification Search
CPC ...................................................... C07H 17/08
USPC .......................................................... 549/271
See application file for complete search history.

(56) References Cited

FOREIGN PATENT DOCUMENTS

| GB | BA 88471 | * | 5/1960 | |
| GB | 884711 | | 12/1961 | |
| JP | B-S34-6000 | * | 1/2006 | |
| KR | 10-2006-0125156 | * | 1/2006 | ............. C07H 17/08 |
| KR | 10-2006-0125156 | | 12/2006 | |

OTHER PUBLICATIONS

Pandey et al., "Physicochemical and Biological Comparison of Polyene Macrolide Antibiotics Fungichromin, Lagosin and Cogomycin," The Journal of Antibiotics, (p. 988-996), (Aug. 1982).
Igarashi et al., "Absolute Configuration of TPU-0043, A Pentaene Macrolide from *Streptomyces* sp.," The Journal of Antibiotics, 58(8) ed., (p. 523-525), (Nov. 2005).
Hsin-Der Shih, et al., "Fungichromin: A Substance from *Streptomyces padanus* with Inhibitory Effects on *Rhizoctonia solani*," Journal of Agricultural and Food Chemistry, 2003 ed., American Chemical Society, (vol. 51), (p. 95-99).

* cited by examiner

*Primary Examiner* — Nizal Chandrakumar
(74) *Attorney, Agent, or Firm* — Hammer & Associates, P.C.

(57) ABSTRACT

Described is pentamycin in a purity exceeding 95%, certain polymorphs and solvates of pentamycin, processes for their manufacture, and a method for decreasing the rate of degradation of pentamycin.

4 Claims, 10 Drawing Sheets

Fig. 1: photo of needles polymorph of pentamycin-morpholine (1:1) solvate

Fig. 2: photo of flake polymorph of pentamycin-morpholine (1:1) solvate

Fig. 3: powder diffraction diagram of needle-shaped pentamycin morpholine solvate Fig. 4: powder X-ray diffraction spectrum of flake shaped pentamycin-morpholine solvate Fig. 5: X-ray of polymorph A of pentamycin Fig. 6: photo of polymorph A of pentamycin Fig. 7: DSC of polymorph A of pentamycin Fig. 8: DSC of amorphous pentamycin Fig. 9 : X-ray powder diffraction diagram of amorphous pentamycin Fig. 10: DSC (above) and X-ray (below) of polymorph C Fig. 11: DSC (above) and X-ray (below) of crude pentamycin Fig. 12: HPLC of crude pentamycin Fig. 13: DSC (above) and X-ray (below) of pentamycin after three crystallizations from methanol as described in J. Antibiotics, ser. A, vol. XI, no.1, Jan. 1958, pp. 26-29

Fig. 14: HPLC of pentamycin after three crystallizations from methanol as described in J. Antibiotics, ser. A, vol. XI, no.1, Jan. 1958, pp. 26-29

HIGHLY PURE PENTAMYCIN

FIELD OF THE INVENTION

The invention relates to highly pure pentamycin, certain polymorphs and solvates of pentamycin, processes for their manufacture, and to a method for decreasing the rate of degradation of more than 95% pure pentamycin.

BACKGROUND OF THE INVENTION

Pentamycin, like Amphotericin B and Nystatin A1, belongs to the class of polyene macrolide antibiotics having antifungal activity. Pentamycin is obtainable from natural sources, e.g. it may be isolated from certain *Streptomyces* strains, like the mycelium of the *actinomyces Streptomyces penticus* as described by S. Umezawa and Y. Tanaka in J. Antibiotics, Ser. A, vol. XI, no. 1, pages 26 to 29 (1958), or from *Streptomyces roseo* luteus (NRRL 2776, NCIB 8984) as described in British patent 884711 to Glaxo. Said patent is directed to the production of the antibiotic lagosin which has been shown in the below-mentioned Pandey et al. article in J. Antibiotics vol. XXXV no. 8, pages 988-996 (1982) to be identical to fungichromin and cogomycin. Lagosin, both as a solid and in solution is stated in said British patent, page 2, right column, lines 48-49, to be sensitive to light.

The absolute configuration of pentamycin (=fungichromin) was determined by spectral comparison of the degradation products and partial synthesis by T. Oishi, Pure & Appl. Chem., vol. 61, no. 3, pp. 427-430 (1989). According to an X-ray analysis published by Y. Igarashi et al. in J. Antibiot. vol. 58, no. 8, pp. 523-525 (2005) pentamycin has the following formula As stated e.g. on page 478, left column, of an article by David R. Worthen et al., Drug Development and Industrial Pharmacy, vol. 27(4), 277-286 (2001) "the production and purification of polyene antifungals are confounded by their inherent chemical instability. The polyenes typically possess one or several potentially unstable structural functionalities, including hydrolyzable esters, acetals, and hemiacetals, as well as conjugated polyene systems vulnerable to oxidation (19). Thus, all of the polyene antifungals, to a certain extent, are subject to inactivation or frank degradation by conditions routinely encountered during their production in and recovery from mass culture. Most notable of these potentially degradative conditions include moisture, elevated temperature, atmospheric oxygen, polyvalent metals, and exposure to light (19, 20)." The references 19 and 20 mentioned in said article are (19) I. M. Teresin, Polyene Antibiotics—Present and Future; University of Tokyo Press: Tokyo, 1976; 122-123, and (20) K. Thoma and N. Kubler, Photostability of antifungal agents. 2. Photostability of polyene antibiotics. Pharmazie vol. 52,294-302 (1997).

The above-mentioned Worthen article goes on by stating on page 478, left column, that "further complicating polyene purification is the fact that virtually all crude polyene isolates from *Streptomyces* contain several distinct, although physicochemically similar, isoforms, only one of which may be desirable for clinical use."

In view of the above, it is not surprising that pentamycin was also given three other names, i.e. lagosin, fungichromin, and cogomycin because they were initially thought to be different substances. As stated by R. C. Pandey et al., J. Antibiotics vol. XXXV no. 8, pages 988-996 (1982) in the abstract "The three polyene macrolide antibiotics, fungichromin, lagosin, and cogomycin, previously described as having some stereochemical differences at one or more centers, are shown by . . . to be identical in all respects, including stereochemical aspects. The differences observed earlier in their properties have now been ascribed to varying amounts of impurities which are separable by high-performance liquid chromatography. All three antibiotics contain one major and several minor components" (emphasis added). In table I on page 988 of said Pandey article the melting points, reported from literature given for fungichromin, lagosin, and cogomycin range from 190 to 240° C.

The Merck Index (12th edition) in entry no. 4312 on page 727 mentions the melting point of fungichromin to be 157-162° C. (decomposition).

The subject of the Pandey article is the physicochemical and biological comparison of said three macrolide antibiotics, not the provision of more than 95% pure pentamycin. As stated on page 995 thereof at the beginning of the "Discussion" it was not possible to remove all the minor components even after repeated CCD (countercurrent distribution) purification. The melting points of the thus purified fungichromin, lagosin, and cogomycin are given in Table 2 on page 990 to range from 157-165° C. Nowhere in the Pandey article it is stated that pentamycin has been isolated or crystallized. The only melting points (ranging from 157 to 240° C.!) given in the Pandey article are those stemming from literature sources in Table 1 and those stemming from countercurrent distribution in Table 2. There is, hence, no indication in the Pandey article that more than 95% pure pentamycin has been obtained.

It should be noted that pentamycin is a comparatively large and structurally complicated molecule containing 12 asymmetric centres so that there are $2^{12}$ (=4096) stereoisomers. In addition, pentamycin contains 5 double bonds which could be subjected to cis-trans-isomerisation. The total chemical synthesis of the right one of the possible 4096 stereoisomers would take years, be an invention on its own, and, from an economic perspective, would be much too costly as compared to the biosynthesis by the *Streptomyces* strains mentioned above, keeping in mind that the stability of pentamycin is very delicate.

The delicate stability of pentamycin is e.g. evident from R. W. Rickards et al., J. Antibiotics vol. XXIII, no. 12, pages 603-611, describing the aerial autooxidation of lagosin in methanol solution by a radical addition process which can be inhibited by antioxidants. According to Rickards et al. the major primary autooxidation products of lagosin are certain epoxides, while extended autooxidation leads to higher oxidation products and ultimately to polymeric materials. In full accordance with the statements in the above-mentioned Worthen article, Rickards et al. state on page 603 that members of the polyene subgroup of macrolide antibiotics "as a whole are unstable, and exposure to acids, alkalis, heat, air or light is accompanied by decomposition and loss of biological activity. In particular, this sensitivity to air and light, which is primarily associated with the polyene chromophore, creates problems in storage prior to clinical use."

The above mentioned British patent 884711 states in Example 1 on page 8, line 41, that "pure lagosin" was obtained. Said Example 1 describes the recovery of lagosin from the fermentation broth comprising the steps of extracting the fermentation broth cuttings with butanol, concentrating the extract, adding water, washing with diethyl ether, filtering, extracting with methanol in a soxhlet and filtering whereupon according to page 8, lines 33 and 35, of the British patent lagosin in a purity of "approximately 75%" is obtained. In order to allegedly remove impurities, the 75% pure lagosin is, as described on page 8, lines 34 to 42, extracted in a soxhlet with chloroform, air dried, extracted with ethyl ether, air dried and reextracted with methanol. On cooling the methanol overnight allegedly "pure lagosin" is obtained, but no melting point is provided.

For a person skilled in the art reading the above passage in the British patent it is extremely doubtful that by the proceedings described above the 75% pure lagosin could, in fact be further purified. This is because the treatment with diethyl ether and methanol has already been effected before without increasing the purity of lagosin above 75%. Hence, why should a repetition of said treatment increase purity substantially? In addition, the steps of drying lagosin in the air would be expected to lead to oxidation as described by Rickards et al. (cf. above). Finally, crystallization of crude pentamycin from methanol does not yield more than 95% pure pentamycin (even three times repetitive crystallisations) as evidenced by Example 8 of the present application. This is because, as was found by the present inventors, certain impurities crystallize together with pentamycin and, hence, cannot be removed by crystallization, but only by other means as described in the present invention. It should be kept in mind that pentamycin is a comparatively large molecule so that the impurities may be distinguished from pentamycin just by a tiny little difference, e.g. epoxidation of one of the five double bonds. Certainly, the separation of compounds which are structurally so close to each other poses enormous problems. Although it could already be expected from the above that no "pure" lagosin can be obtained by the procedure of Example 1 of the British patent 884,711, the applicants of the present invention ordered an outside institute to repeat the process described in said Example as closely as possible. The result is described in Example 10 of the present application. As expected, while the purity of "approximately 75%" for the intermediate material could be roughly confirmed (found: 67.3%), the further purification steps did not yield "pure" pentamycin, but only pentamycin in a purity of 70.1%.

Pentamycin was the active ingredient in a drug registered in the 1980s under the trade name Pentacin® in Switzerland, but, due to difficulties in meeting the registered product specifications for purity and stability (even though the marketed formulation contained an antioxidant), was withdrawn from the market. According to the specification in the Swiss registration documents the purity of pentamycin was 95%. However, when using the modern means of analysis available today, it now turned out that a number of impurities present in pentamycin as registered in the past had not been detected and that, hence, the actual purity of pentamycin in the past was much lower than 95%.

Pentamycin itself has a lipophilic and a very hydrophilic part and thus behaves similar to a surfactant. Furthermore it is relatively insoluble in water and tends to form gels, which are almost unfilterable.

Despite intensive efforts, the present inventors were not able to increase the purity of pentamycin above 93% for a long time. In fact, the purity threshold of 93% appeared to be unsurmountable until the present invention.

The problem to be solved by the present inventors was to increase the purity of pentamycin above 93%, especially above 95%, and to bring pentamycin into a form stable enough to enable its reintroduction into the pharmaceutical market in Switzerland and its registration as a drug in other countries.

DESCRIPTION OF THE INVENTION

After long and initially fruitless efforts, it has now surprisingly been found by the inventors of the present patent application how pentamycin can be manufactured in a purity exceeding 93%, especially exceeding 95%, and successfully stabilized against degradation.

The present inventors discovered that certain impurities appear to crystallize together with pentamycin in the same crystal lattice so that further purification by crystallization proved to be impossible. As shown in Example 8, even after three consecutive crystallizations of crude pentamycin from methanol the obtained product still contains about 10% of impurities. Said impurities comprise compounds which are structurally very similar to pentamycin so that they can not all be removed by simple conventional means, e.g. various epoxides of pentamycin, pentamycin derivatives wherein a hydroxy group is replaced by an oxo group or methylated to a methoxy group, pentamycin derivatives wherein a double bond is reduced to a single bond, pentamycin derivatives which contain a tetrahydropyranone ring, and/or, potentially, stereoisomers of pentamycin.

It was now found that pentamycin forms certain solvates with small polar heterocycles, like morpholine (1:1 molar ratio), N-methylpyrrolidone (NMP; 1:1 molar ratio), M-ethylpyrrolidone (NEP), or tetrahydrofuran (THF), preferably in alcoholic solvents like methanol or ethanol, and that some of those solvates, e.g. the solvates with NMP and especially morpholine, have useful properties, i.e. they can surprisingly be used to purify pentamycin above the threshold of 93% when manufacturing them in methanol or ethanol, but, according to present experience, not in unpolar solvents, like methyl tertiary butyl ether (MTBE) or toluene. In the context of the present text the term "solvate" is to be understood as comprising also a cocrystal since the difference between a solvate and a cocrystal resides merely in whether the above-mentioned small polar heterocycle is liquid or solid at room temperature.

Hence, the invention relates to a process for the manufacture of pentamycin in a chemical purity exceeding 93%, preferably 95%, more preferably 96% and most preferably 97% by weight and to certain solvates and polymorphs of pentamycin and their use for purifying and or stabilizing pentamycin.

The present inventors conducted a high number of crystallization experiments wherein pentamycin was dissolved e.g. in dimethyl sulfoxide (DMSO), dimethyl formamide (DMF), and N-methylpyrrolidone (NMP). To the thus obtained solution were then added anti-solvents until crystallization occurred, anti-solvents meaning solvents wherein pentamycin is considerably less soluble, like methanol, ethanol, isopropanol, acetone, ethyl acetate, or acetonitrile. Crystallizations of pentamycin dissolved in a high volume of anti-solvents, like methanol, were also tested.

During the course of said crystallization experiments it was discovered that pentamycin forms solvates with morpholine and N-methylpyrrolidone, but not with DMSO, and that said solvates can surprisingly be used to reduce the impurities co-crystallizing with pentamycin by way of repeated recrystallization of said solvates.

Figure 1:
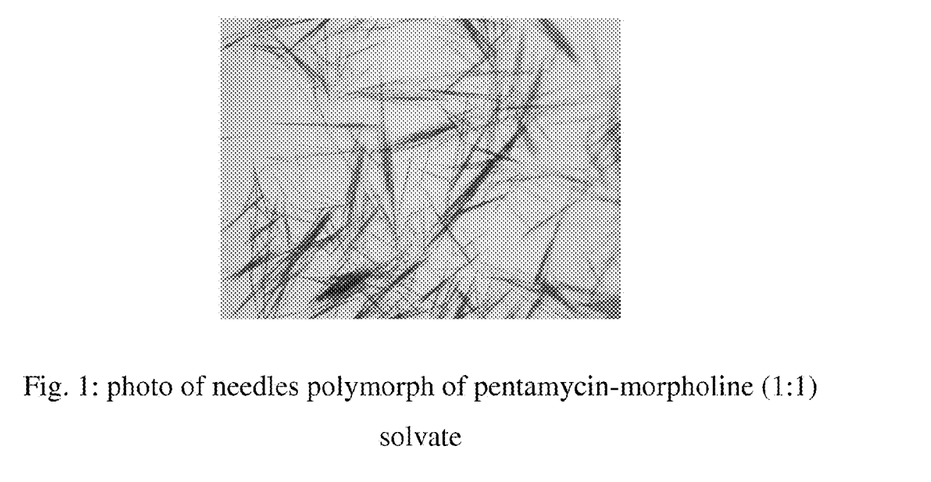
FIG. 1 shows a photograph of needle-shaped pentamycin morpholine (1:1) solvate.
Figure 2:
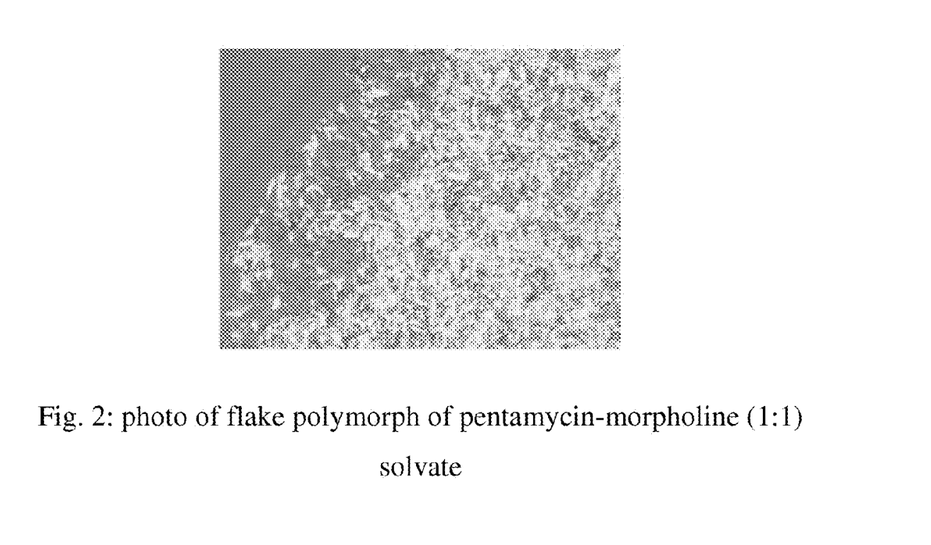
FIG. 2 shows a photograph of flake-shaped pentamycin morpholine (1:1) solvate.

One method of removing the impurities co-crystallizing with pentamycin is to successively manufacture and crystallize a solvate of pentamycine with morpholine which first crystallizes in the form of needles (cf. FIG. 1), then to transform the needle-shaped polymorphic morpholine solvate into a morpholine solvate which crystallizes in the form of flakes (cf. FIG. 2), and then to remove the morpholine. In comparison to the flake-shaped pentamycin morpholine solvate the needle-shaped solvate is less suitable for purification. According to the (still limited) experimental experience obtained so far it can not be purified above a threshold well above 93% by recrystallizations. Therefore, the needle-shaped solvate is transformed as soon as possible into the flake-shaped solvate, e.g. by addition of seed crystals of the flake-shaped solvate. The successive manufacture of the needle- and flake-shaped morpholine solvates can be performed in one pot. The manufacture of the morpholine solvates is preferably conducted under protecting gas, like nitrogen, protected from light, and in the presence of an anti-oxidant, like butylated hydroxy-anisole (BHA) or, preferably, butylated hydroxy-toluene (BHT), i.e. 2,6-ditertiarybutyl-4-methyl phenol. The crystallization is preferably carried out in suitable polar solvents, like a suitable alcohol, e.g. a suitable alkanol, e.g. ethanol or most preferably methanol. With longer alcohols and unpolar solvents, e.g. toluene, MTBE, etc. almost no purification effect is achieved. Morpholine as a single solvent is also not advantageous, because the solubility of pentamycin is too high in morpholine. The purification by formation of the flake-shaped morpholine solvate is repeated as many times as needed to obtain the desired purity.

Increasing the amount of morpholine relative to pentamycin in the solvent system accelerates the transformation of the needle-shaped polymorph into the flake-shaped polymorph. As stated above, said transformation can also be accelerated by adding seed crystals of the flake-shaped polymorph.

The invention relates to a process of purifying crude pentamycin through formation of its flake-shaped morpholine solvate (1:1 molar ratio of pentamycin and morpholine) by stirring a mixture of crude pentamycin, a suitable alcohol, like especially a lower alkanol, like ethanol or, preferably methanol, morpholine, and a suitable anti-oxidant, like BHT, at a temperature between preferably about 5 and 50° C., preferably at room temperature, advantageously under a protecting gas, like nitrogen, until the flake-shaped pentamycin-morpholine solvate has crystallized, isolating it, e.g. by filtration and washing with a lower alkanol, like methanol, and, if desired, further purifying the obtained flake-shaped pentamycin-morpholine solvate by repeating the above procedure one or more times using the obtained flake-shaped pentamycin-morpholine solvate instead of the crude pentamycin.

The invention relates also to a process of purifying crude pentamycin through formation of its NMP solvate by stirring a mixture of crude pentamycin, a suitable alcohol, like especially a lower alkanol, like ethanol or, preferably methanol, N-methylpyrrolidone (NMP), and a suitable anti-oxidant, like BHT, at a temperature between preferably about 5 and 50° C., preferably at room temperature, advantageously under a protecting gas, like nitrogen, until NMP solvate has crystallized, isolating it, e.g. by filtration and washing with a lower alkanol, like methanol, and, if desired, further purifying the obtained NMP solvate by repeating the above procedure.

By the above process using the NMP solvate one of two impurities co-crystallizing with pentamycin, i.e. the impurity (imp) at a relative retention time (rrt) of 1.54 (in the HPLC system described herein) can be removed while another impurity at rrt of 0.83 is only reducible to a level of 3.3%.

Morpholine and NMP are removed from the respective pentamycin solvates by stirring the solvates for several hours in methanol or preferably ethanol, e.g. at a temperature between 0° C. and +50° C., preferably at room temperature, filtering the obtained crystals, washing them with methanol or preferably ethanol, and, if desired, repeating the process until the obtained product comprises less than 0.1% of morpholine or NMP.

The residual morpholine or NMP can be removed by crystallization from DMSO/ethanol or DMSO/methanol, whereby polymorph A of pentamycin is obtained.

Figure 8:
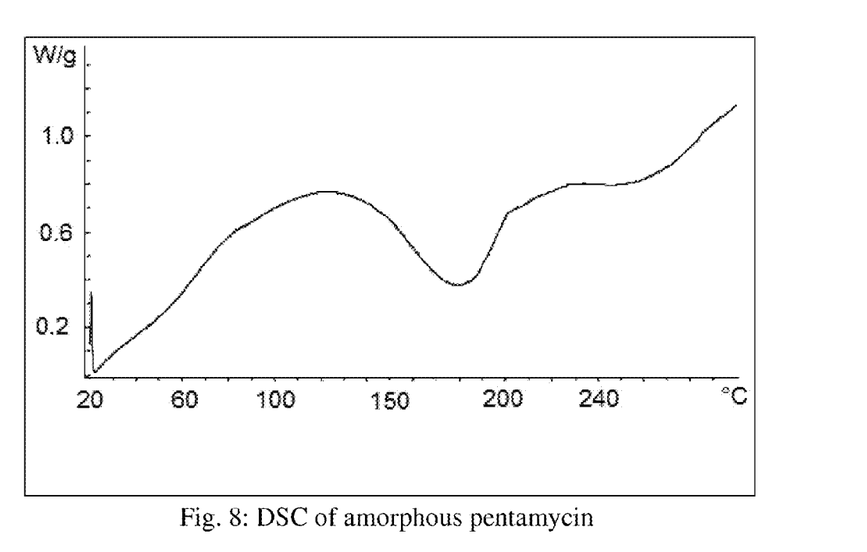
FIG. 8 shows the DSC of amorphous pentamycin.
Figure 9:
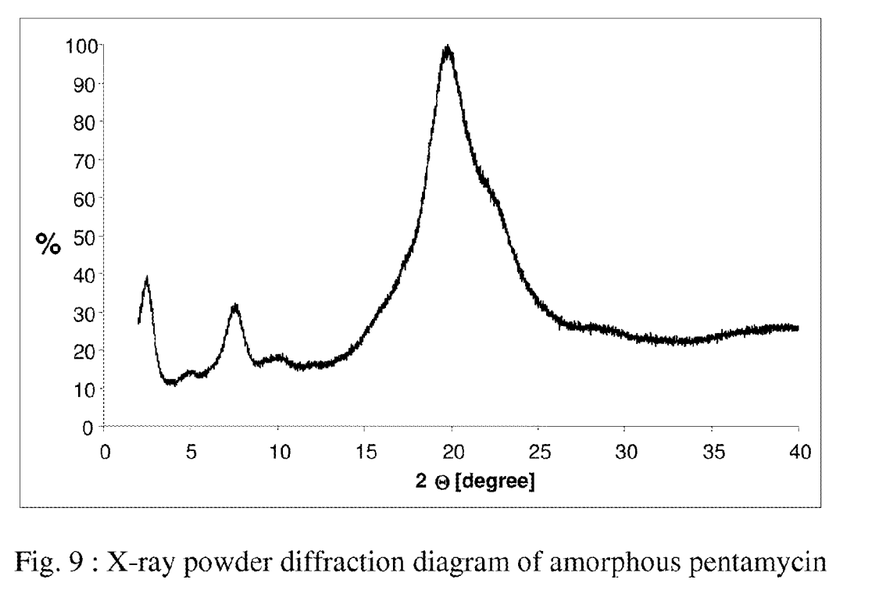
FIG. 9 shows a powder X-ray diffraction diagram of amorphous pentamycin.

It was found that pentamycin exists in an amorphous form (cf. FIG. 8 and FIG. 9) and several other polymorphic forms besides form A, hereinafter named polymorphs B to E. As compared to the other polymorphs, polymorph A is distinguished in the powder diffraction X-ray by lines at the following 2theta angles (±about 0.2°): 2.28, 7.38 and 20.16, polymorph B gives rise to lines at 9.54, 21.28 and 22.32, polymorph C has a characteristic line at 7.04, polymorph D has a characteristic line at 2.58, polymorph E has a characteristic, although not very intensive line at 3.32, and crude pentamycin (cf. FIG. 11 and FIG. 12) exhibits characteristic lines at 8.84 and 13.14. When comparing the above-mentioned 2theta angles (±about 0.2°): 2.28, 7.38 and 20.16 for polymorph A with the corresponding values in Example 7, i.e. 2.22, 7.29 and 20.17, the small discrepancy is evident. It is due to the fact that the respective figures stem from different measurements. The differences are, however, well within the internationally accepted experimental error for 2theta angles of ±0.2°.

Polymorph A crystallizes e.g. from a solution of pentamycin in dimethylsulfoxide (DMSO) after adding ethyl acetate.

Amorphous pentamycin is obtained e.g. from a solution of pentamycin in dimethylsulfoxide (DMSO) after adding acetonitrile.

Polymorph B crystallizes from methanol/chloroform.

Figure 10:
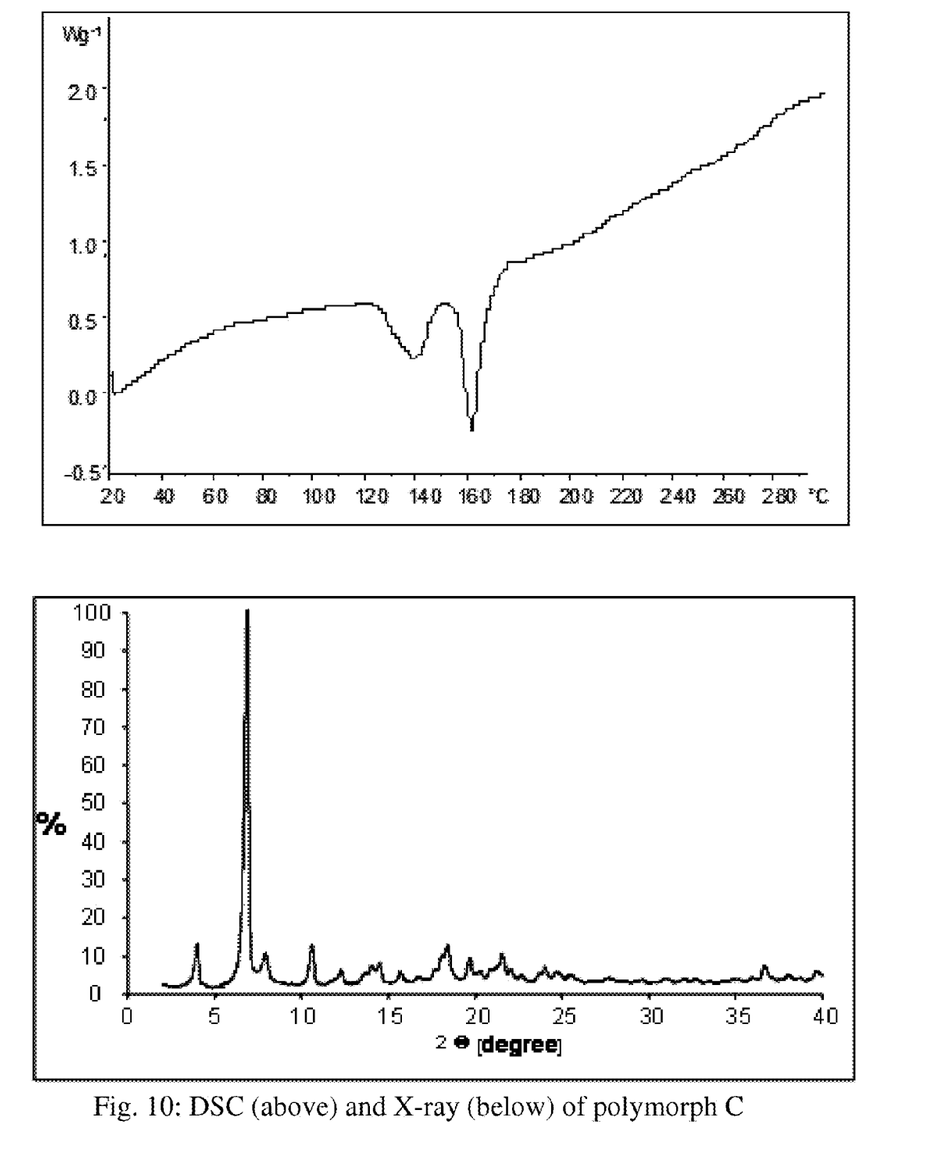
FIG. 10 shows the DSC (above) and X-ray (below) of polymorph C of pentamycin.

Polymorph C (cf. FIG. 10) is obtained by adding methanol to a solution of pentamycine in dimethylformamide at 60° C., adding methanol and cooling down to 0° C.

Polymorph E crystallizes from dimethylsulfoxide/acetonitril.

Polymorph A appears to be the thermodynamically most stable polymorph. Its differential scanning calorimetry (DSC) diagram (depicted in FIG. 7) exhibits one single signal. In contrast thereto the DSC-diagrams of the other crystalline polymorphs show more than one signal (cf. e.g. the DSC of polymorph C in FIG. 10), thus indicating transitions into other polymorphic forms when gradually increasing the temperature. The most surprising and quite unforeseeable quality of pure polymorph A is its stability on exposure to air (cf. Example 9) which is quite in contrast to all forms of pure pentamycin known so far.

The highly pure forms of pentamycin of the present invention, like especially polymorph A of pentamycin in a chemical purity exceeding 95%, can be used in a method of treating warm-blooded animals, including preferably mammals and especially humans, e.g. in the form of pharmaceutical formulations for topical use, e.g. vaginal suppositories, to treat vaginal and mucosa infections caused by *Candida*, especially *Candida albicans*, and *Trichomonas vaginalis*.

Said pharmaceutical formulations for topical use, e.g. vaginal suppositories, comprise e.g. pentamycin in a concentration of 0.1 to 5% by weight together with suitable pharmaceutical excipients and contain from 3 mg to 150 mg of pentamycin per dosage unit, i.e. suppository. The vaginal suppositories are supplied e.g. to a female human of about 60 kg body weight 1-2 times daily.

Summarizing, the present invention relates to pentamycin in a chemical purity exceeding 95%, preferably in a chemical purity exceeding 97%, especially in the form of polymorph A, more especially in the form of polymorph A in a chemical purity exceeding 95%, preferably 97%, characterized by the following 2theta values, ±about 0.2°, of the most intense lines in the X-ray powder diffraction spectrum, the relative intensities being provided as rough indication only:

| 2Theta angle | relative intensity | 2Theta angle | relative intensity | 2Theta angle | relative intensity | 2Theta angle | relative intensity |
|---|---|---|---|---|---|---|---|
| 2.22 | 100 | 7.29 | 33 | 9.25 | 15 | 19.78 | 51 |
| 20.17 | 52 | 20.62 | 25 | 21.24 | 17 | | |

The present invention relates further to pentamycin in the form of a solvate, especially in the form of a solvate which is suitable for purification of pentamycin, like such solvate with a heterocyclic compound, preferably with a low-molecular weight heterocyclic compound, e.g. N-methyl-pyrrolidone or preferably morpholine, like the needle shaped morpholine solvate, or preferably the flake shaped morpholine solvate, especially to such solvate in a chemical purity exceeding 95%, 96%, or preferably 97%, especially the flake shaped morpholine solvate having the following 2theta values, ±about 0.2°, of the most intense lines in the powder X-ray diffraction spectrum, the relative intensities being provided as rough indication only:

| 2Theta angle | Relative intensity | 2Theta angle | Relative intensity | 2Theta angle | Relative intensity |
|---|---|---|---|---|---|
| 9.73 | 41.5 | 21.49 | 68.5 | 28.95 | 12.0 |
| 10.29 | 17.1 | 22.08 | 16.5 | 29.33 | 12.2 |
| 12.99 | 14.0 | 22.47 | 26.9 | 30.32 | 10.8 |
| 15.04 | 24.7 | 23.02 | 24.5 | 34.02 | 10.1 |
| 16.01 | 15.1 | 24.06 | 13.4 | 35.24 | 12.1 |
| 17.29 | 19.3 | 25.21 | 10.7 | 35.81 | 11.5 |
| 18.29 | 18.2 | 25.91 | 16.0 | 36.37 | 10.7 |
| 19.26 | 28.0 | 26.55 | 18.5 | 37.42 | 13.1 |
| 20.03 | 92.3 | 27.79 | 12.7 | 37.91 | 12.6 |
| 20.67 | 100.00 | 28.09 | 12.7 | 39.39 | 14.1 |

The present invention relates further to the use of the above-mentioned pentamycin solvates for the chemical purification of pentamycin.

The present invention relates further to a process for purification of pentamycin by transforming pentamycin in a chemical purity below 93% into a suitable solvate, especially one of the above-mentioned solvates, purifying said solvate by crystallization, and freeing pentamycin from the solvate, e.g. by prolonged stiffing in a $C_{1-5}$-alkanol, said purification process being, if desired, carried out in the presence of a suitable antioxidant, like preferably 2,6-ditertiarybutyl-4-methyl phenol.

The present invention relates further to a method for significantly decreasing the rate of degradation of pentamycin in a chemical purity exceeding 95% by transforming it into the form of its polymorph A, especially to such method wherein the transformation into polymorph A is effected by crystallizing it from a solution of more than 95% pure pentamycin in dimethylsulfoxide after adding ethyl acetate.

DETAILED DESCRIPTION OF EXPERIMENTS

The powder X-ray spectra are recorded on a Rigaku Miniflex diffractometer (copper Ka radiation, recording range 2-40° [2Theta], step width 0.02° [2Theta], recording interval 0.0083° [2Theta], probe container: silicon). The experimental error in recorded 2Theta angles is about ±0.2°. The experimental error in relative intensities is high. Hence, relative intensities should be understood as being roughly indicative only.

The following examples illustrate the invention. The abbreviation "rrt" means "relative retention time", i.e. the ratio between the net retention time of an impurity and that of a pentamycin in HPLC (High Performance Liquid Chromatography). The term "imp rrt" used in the examples means the retention time of an impurity relative to pentamycin, i.e. the rrt of pentamycin is 1.00. Relative retention times below 1.00 mean that the impurity is eluted earlier than pentamycin, relative retention times greater than 1.00 mean that the impurity is eluted after pentamycin. For example "imp rrt=0.83: 8.0%" means that there is an impurity in the amount of 8% at a relative retention time of 0.83. As customary in HPLC the percentages of the detected compounds are expressed as area percent reflecting the area of the respective signal, i.e. in the above example the 8.0% are area percent. The HPLC chromatography described herein is carried out using an Agilent (trade mark) 1100 system or equivalent. The mobile phase comprises solutions A and B, solution A being water-acetonitrile-trifluoroacetic acid in the ratio 650:350:0.01 (v:v:v), solution B being acetonitrile-2-propanol-trifluoroacetic acid in the ratio 750:250:0.01 (v:v:v). The sample to be analysed is dissolved in acetonitrile-water-tetrahydrofuran in the ratio 1:1:2 (v:v:v) to which 0.1% (w:v) of BHT in acetonitrile-water-tetrahydrofuran in the ratio 1:1:2 (v:v:v) are added and tested in a final concentration of 0.6 mg/ml.

The HPLC is conducted on a Waters Atlantis (trade mark) dC$_{18}$ RP 250×4.6 mm, 5 µm column Atlantis dC$_{18}$ columns are a silica-based line of difunctionally bonded reversed-phase C$_{18}$ columns The following parameters are used:

Gradient:

| Time [minutes] | Solution A [% by volume] | Solution B [% by volume] |
|---|---|---|
| 0 | 100 | 0 |
| 6 | 100 | 0 |
| 10 | 77 | 23 |
| 16 | 77 | 23 |
| 17 | 40 | 60 |
| 22 | 40 | 60 |
| 23 | 100 | 0 |
| 30 | 100 | 0 |

Flow rate: 1.0 ml/min
Temperature: 40° C.
Detection: 320 nm
Injection volume: 5 µl

EXAMPLES

Example 1

Needle-Shaped Pentamycin-Morpholine Solvate

To a mixture of methanol (1.75 g) and morpholine (0.75 g) is added butylated hydroxytoluene (BHT; 2,6-ditertiarybutyl-4-methyl phenol) (4 mg) and crude pentamycin (500 mg; chemical purity: 80.6%); pentamycin content: 80%; imp rrt=0.83:8.0%; imp rrt=1.54:7.0%). The HPLC chromatogram of the crude pentamycin shows 2 major peaks caused by impurities. The first has a relative retention time (rrt) of 0.83. This peak consists of (at least) 2 different impurities with the same retention time. The total amount of these 2 impurities together is 8%. The second major impurity has a rrt of 1.54 and the quantity of this impurity in the starting material is 7%.

The mixture is stirred at room temperature for 3 days. The crystals are filtered, washed with methanol (2 times 1 ml) and dried under reduced pressure to yield needle-shaped pentamycin-morpholine solvate (362 mg; chemical purity: 86.2%; pentamycin content: 75%; morpholine content: 10%; imp rrt=0.83:5.3%; imp rrt=1.54:6.5%).

As evident from the above, the amount of both the impurities at rrt 0.83 and rrt 1.54 are reduced in the needle-shaped pentamycin-morpholine solvate as compared to the crude pentamycin used as starting material.

Example 2

Flake-Shaped Pentamycin-Morpholine Solvate (1:1 Molar Ratio)

To a mixture of methanol (1.5 g) and morpholine (1 g) are added BHT (4 mg) and crude pentamycin (500 mg; chemical purity: 80.6%; pentamycin content: 80%; imp rrt=0.83:8.0%; imp rrt=1.54:7.0%). The mixture is stirred at room temperature for 3 days. The crystals are filtered, washed with methanol (2 times 1 ml) and dried under reduced pressure to yield flake-shaped pentamycin-morpholine solvate (327 mg; chemical purity: 90.9%; pentamycin content: 82%; imp rrt=0.83:4.3%; imp rrt=1.54:3.0%) containing pentamycin and morpholine in a 1:1 molar ratio.

Note: After 30 minutes stirring time mainly the needle-shaped polymorph is observed under the microscope. After 3 days stirring time, the crystal form change to a "flake" shape.

As evident from the above, the amount of both the impurities at rrt 0.83 and rrt 1.54 is further reduced in the flake-shaped pentamycin-morpholine solvate as compared to both the crude pentamycin used as starting material and the needle-shaped polymorph described in Example 1.

Figure 3:
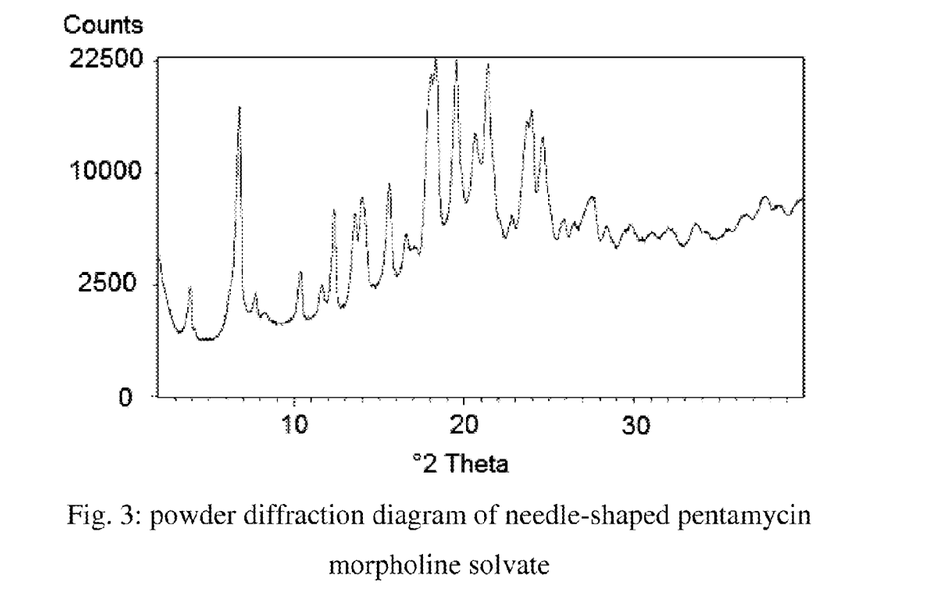
FIG. 3 shows a powder diffraction diagram of needle-shaped pentamycin morpholine (1:1) solvate.

The powder X-ray diffraction spectrum of the needle-shaped polymorph of pentamycin-morpholine solvate (1:1 molar ratio) is depicted in FIG. 3.

Example 3

Manufacture of Flake-Shaped Pentamycin-Morpholine Solvate Using Seed Crystals

To a mixture of methanol (11.52 g) and morpholine (7.68 g) are added BHT (10 mg) and crude pentamycin (4.0 g; chemical purity: 80.6%; pentamycin content: 80%; imp rrt=0.83:8.0%; imp rrt=1.54:7.0%). The mixture is seeded with seeding crystals of the flake shaped pentamycin morpholine solvate (12 mg; flake-polymorph) and stirred at room temperature for 10 h. Then another portion of crude pentamycin (2.4 g) is added and the mixture is stirred over night. The crystals are filtered, washed with methanol (3 times 3 ml) and dried under reduced pressure to yield pentamycin. (5.46 g; chemical purity: 89.2%; pentamycin content: 82%; imp rrt=0.83:4.9%; imp rrt=1.54:4.0%; content corrected yield: 78%; yield of theory: 87%).

Example 4

Purification of the Flake-Shaped Pentamycin-Morpholine Solvate

To a mixture of methanol (20.6 g) and morpholine (13.7 g) is added BHT (4 mg) and flake-shaped pentamycin-morpholine solvate (4.75 g; chemical purity: 89.2%; pentamycin content: 81%; imp rrt=0.83:4.9%; imp rrt=1.54:4.0%). The mixture is stirred at room temperature for 16 hours. The crystals are filtered, washed with methanol (2 times 2 ml) and dried under reduced pressure to yield purified flake-shaped pentamycin-morpholine solvate (3.45 g). A part of this material (3.39 g) is added to a mixture of methanol (10.8 g), morpholine (7.2 g) and BHT (4 mg). The mixture is stirred at room temperature for 16 hours. The crystals are filtered, washed with methanol (2 times 1 ml) and dried under reduced pressure to yield further purified flake-shaped pentamycin-morpholine solvate (2.27 g; chemical purity: 93.7%; pentamycin content: 83%; imp rrt=0.83:3.2%; imp rrt=1.54:2.0%).

Example 5

Successive Recrystallizations of the Flake-Shaped Pentamycin-Morpholine Solvate

To a mixture of methanol (1.5 g) and morpholine (1.0 g) are added BHT (5 mg) and flake shaped pentamycin morpholine solvate (385 mg; chemical purity: 87.7%; pentamycin content: 80%; imp rrt=0.83:5.4%; imp rrt=1.54:4.7%). The mixture is stirred at room temperature for 18 h. The crystals are filtered, washed with methanol (3 times 0.5 ml) and dried under reduced pressure to yield flake shaped pentamycin morpholine solvate (230 mg; chemical purity: 94.5%; imp rrt=0.83:3.0%; imp rrt=1.54:1.5%).

To a mixture of methanol (0.84 g) and morpholine (0.56 g) are added BHT (3 mg) and flake shaped pentamycin morpholine solvate (220 mg; chemical purity: 94.5%; imp rrt=0.83: 3.0%; imp rrt=1.54:1.5%). The mixture is stirred at room temperature for 18 h. The crystals are filtered, washed with methanol (3 times 0.5 ml) and dried under reduced pressure to yield flake shaped pentamycin morpholine solvate (144 mg; chemical purity: 96.2%; imp rrt=0.83:2.3%; imp rrt=1.54: 0.82%).

To a mixture of methanol (0.6 g) and morpholine (0.4 g) are added BHT (2 mg) and flake shaped pentamycin morpholine solvate (244 mg; chemical purity: 96%; imp rrt=0.83:2.3%; imp rrt=1.54:1.0%). The mixture is stirred at room temperature for 18 h. The crystals are filtered, washed with methanol (3 times 0.5 ml) and dried under reduced pressure to yield flake shaped pentamycin morpholine solvate pentamycin (162 mg; chemical purity: 96.6%; imp rrt=0.83:1.9%; imp rrt=1.54:0.7%).

To a mixture of methanol (0.42 g) and morpholine (0.28 g) are added BHT (2 mg) and flake shaped pentamycin morpholine solvate (140 mg; chemical purity: 96.6%; imp rrt=0.83: 1.9%; imp rrt=1.54:0.7%). The mixture is stirred at room temperature for 18 h. The crystals are filtered, washed with methanol (3 times 0.5 ml) and dried under reduced pressure to yield flake shaped pentamycin morpholine solvate (89 mg; chemical purity: 97.3%; imp rrt=0.83:1.6%; imp rrt=1.54: 0.5%).

Figure 4:
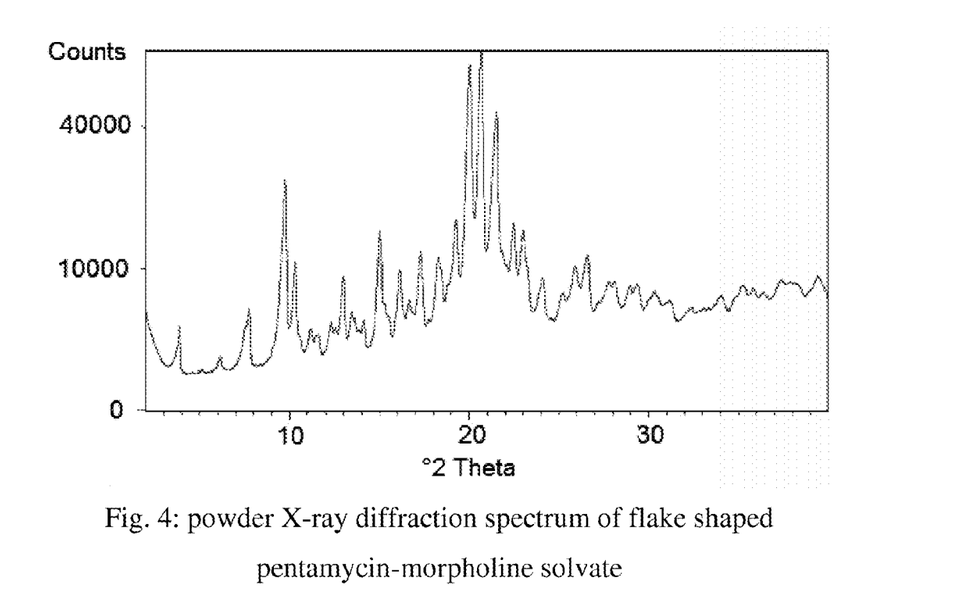
FIG. 4 shows a powder X-ray diffraction spectrum of flake shaped pentamycin-morpholine (1:1) solvate.

The powder X-ray diffraction spectrum of the obtained flake-shaped polymorph of pentamycin-morpholine solvate (1:1 molar ratio) is depicted in FIG. 4. The 2theta angles [degrees], ±about 0.1°, and relative intensities [%] of the most intense lines are as follows:

| 2Theta angle | Relative intensity | 2Theta angle | Relative intensity | 2Theta angle | Relative intensity |
|---|---|---|---|---|---|
| 9.73 | 41.5 | 21.49 | 68.5 | 28.95 | 12.0 |
| 10.29 | 17.1 | 22.08 | 16.5 | 29.33 | 12.2 |
| 12.99 | 14.0 | 22.47 | 26.9 | 30.32 | 10.8 |
| 15.04 | 24.7 | 23.02 | 24.5 | 34.02 | 10.1 |
| 16.01 | 15.1 | 24.06 | 13.4 | 35.24 | 12.1 |
| 17.29 | 19.3 | 25.21 | 10.7 | 35.81 | 11.5 |
| 18.29 | 18.2 | 25.91 | 16.0 | 36.37 | 10.7 |
| 19.26 | 28.0 | 26.55 | 18.5 | 37.42 | 13.1 |
| 20.03 | 92.3 | 27.79 | 12.7 | 37.91 | 12.6 |
| 20.67 | 100.00 | 28.09 | 12.7 | 39.39 | 14.1 |

As evident from the above, the amount of both the impurities at rrt 0.83 and rrt 1.54 are further reduced in the purified flake-shaped pentamycin-morpholine solvate as compared to both the crude pentamycin used as starting material, the needle-shaped polymorph described in Example 1 and the crude flake-shaped pentamycin-morpholine solvate described in Example 2.

Example 6

Pentamycin-N-methylpyrrolidone Solvate (1:1 Molar Ratio)

Steps 6.1 to 6.8 show the manufacture of the above mentioned solvate and its purification by repeated crystallization. As evident therefrom, the imp rrt=1.54 is efficiently removed, but the other major imp. rrt=0.83 is only reducible to a level of 3.3%.

Step 6.1: Manufacture of Pentamycin-NMP-Solvate

To a mixture of methanol (65 g) and N-methylpyrrolidone (NMP; 65 g) are added BHT (100 mg) and crude pentamycin (20 g; chemical purity: 80.6%; pentamycin content: 80%; imp rrt=0.83:8.0%; imp rrt=1.54:7.0%). The mixture was stirred at room temperature for 5 hours. The crystals are filtered, washed with methanol (2 times 10 ml) and dried under reduced pressure to yield pentamycin-NMP-solvate (17.3 g; chemical purity: 86.9%; pentamycin content: 71%; imp rrt=0.83:5.8%; imp rrt=1.54:5.0%).

Step 6.2: First Recrystallization of Pentamycin-NMP-Solvate

To a mixture of methanol (50 g) and NMP (50 g) are added BHT (100 mg) and pentamycin-NMP-solvate from step 6.1 (17.3 g; chemical purity: 86.9%; pentamycin content: 71%; imp rrt=0.83:5.8%; imp rrt=1.54:5.0%). The mixture is stirred at room temperature for 18 hours. The crystals are filtered, washed with methanol (2 times 10 ml) and dried under reduced pressure to yield pentamycin-NMP solvate (9.7 g; chemical purity: 91.5%; pentamycin content: 81%; imp rrt=0.83:4.3%; imp rrt=1.54:2.9%).

Step 6.3: Second Recrystallization of Pentamycin-NMP-Solvate

To a mixture of methanol (30 g) and NMP (30 g) are added BHT (100 mg) and pentamycin NMP-solvate from step 6.2 (9.65 g). The mixture is stirred at room temperature for 5 hours. The crystals are filtered, washed with methanol (2 times 10 ml) and dried under reduced pressure to yield pentamycin-NMP solvate (7.5 g; chemical purity: 93.5%; pentamycin content: 83%; imp rrt=0.83:3.8%; imp rrt=1.54:1.9%).

Step 6.4: Third Recrystallization of Pentamycin-NMP-Solvate

To a mixture of methanol (22 g) and NMP (22 g) are added BHT (100 mg) and pentamycin NMP-solvate from step 6.3 (7.45 g. The mixture is stirred at room temperature for 18 hours. The crystals are filtered, washed with methanol (2 times 10 ml) and dried under reduced pressure to yield pentamycin-NMP solvate (4.0 g; chemical purity: 94.9%; pentamycin content: 87%; imp rrt=0.83:3.5%; imp rrt=1.54:1.2%).

Step 6.5: Fourth Recrystallization of Pentamycin-NMP-Solvate

To a mixture of methanol (12 g) and NMP (12 g) are added BHT (50 mg) and pentamycin NMP-solvate from step 6.4 (3.6 g). The mixture is stirred at room temperature for 3 days. The crystals are filtered, washed with methanol (2 times 5 ml) and dried under reduced pressure to yield pentamycin-NMP solvate (2.78 g; chemical purity: 95.8%; pentamycin content: 86%; imp rrt=0.83:3.3%; imp rrt=1.54:0.5%).

Step 6.6: Fifth Recrystallization of Pentamycin-NMP-Solvate

To a mixture of methanol (8 g) and NMP (8 g) are added BHT (50 mg) and pentamycin-NMP-solvate from step 6.5 (2.5 g). The mixture is stirred at room temperature for 4 hours. The crystals are filtered, washed with methanol (2 times 4 ml) and dried under reduced pressure to yield pentamycin-NMP solvate (3.1 g; chemical purity: 95.8%; pentamycin content: 71% (due to residual solvent); imp rrt=0.83:3.3%; imp rrt=1.54:0.4%).

Step 6.7: Sixth Recrystallization of Pentamycin-NMP-Solvate

To a mixture of methanol (6 g) and NMP (6 g) are added BHT (50 mg) and pentamycin NMP-solvate from step 6.6 (2.3 g). The mixture is stirred at room temperature for 18 hours. The crystals are filtered, washed with methanol (2 times 3 ml) and dried under reduced pressure to yield pentamycin-NMP solvate (1.6 g; chemical purity: 96.0%; pentamycin content: 88%; imp rrt=0.83:3.3%; imp rrt=1.54:0.3%).

As evident from steps 6.5 to 6.7 the amount of the impurity present at relative retention time 0.83 remained at 3.3% and could not be further reduced.

Example 7

Manufacture of Polymorph A of Pentamycin from Pentamycin-Morpholine Solvate

To flake-shaped pentamycin morpholine solvate (1.5 g; content of morpholine: 8%; chemical purity: 97.2%) are added ethanol (13 g) and BHT (5 mg) and the mixture is stirred at room temperature for 2 hours. The crystals are filtered and washed with ethanol (3 times 2 ml). To the crystals are added again ethanol (13 g) and BHT (5 mg) and the mixture is stirred at room temperature for 2 hours. The crystals are filtered, washed with ethanol (3 times 2 ml) and dried under reduced pressure to yield pentamycin (1.1 g; content of morpholine: <0.1%; chemical purity: 97.3%).

Figure 6:
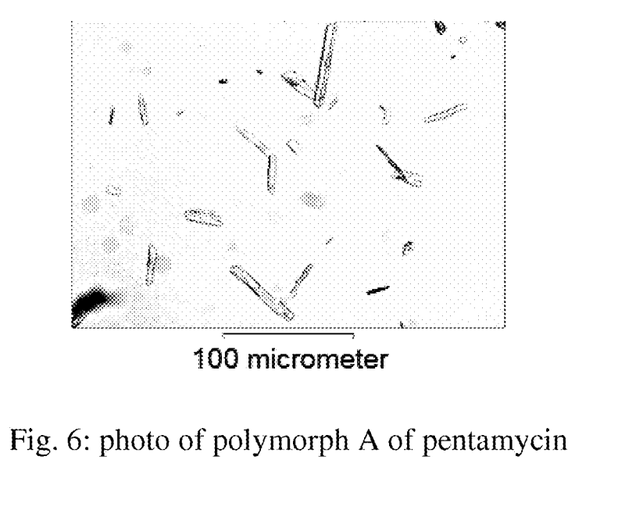
FIG. 6 shows a photo of polymorph A of pentamycin.

The obtained product is dissolved in DMSO at 80° C. under nitrogen and crystallized by slow addition of methanol or ethanol, cooling to 0° C., filtering the obtained crystals and washing them with methanol or ethanol whereupon polymorph A of pentamycin is obtained. A photo of the crystals is depicted in FIG. 6.

Figure 7:
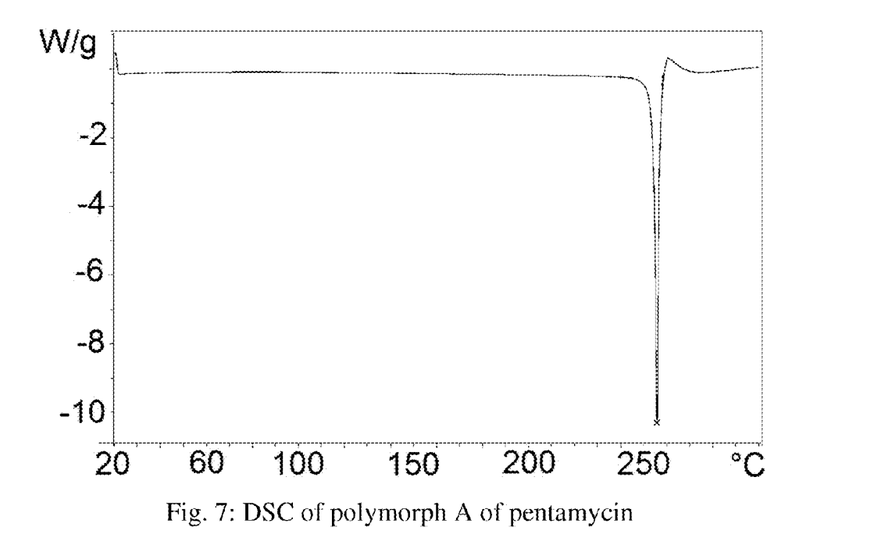
FIG. 7: shows the differential scanning calorimetry (DSC) diagram of polymorph A of pentamycin.

The DSC of polymorph A of pentamycin is depicted in FIG. 7 (onset at 253.7; peak at 254.4° C.).

Figure 5:
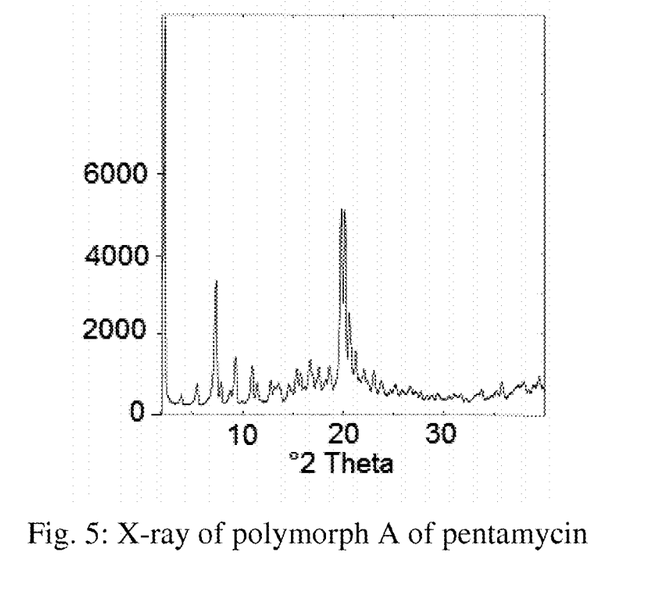
FIG. 5 shows a powder X-ray diffraction diagram of polymorph A of pentamycin.

The powder X-ray diffraction spectrum of polymorph A of pentamycin is depicted in FIG. 5.

The 2Theta angles [degrees], ±about 0.2°, and relative intensities [%] of the most intense lines are as follows:

| 2Theta angle | relative intensity | 2Theta angle | relative intensity | 2Theta angle | relative intensity | 2Theta angle | relative intensity |
|---|---|---|---|---|---|---|---|
| 2.22 | 100 | 7.29 | 33 | 9.25 | 15 | 19.78 | 51 |
| 20.17 | 52 | 20.62 | 25 | 21.24 | 17 | | |

Example 8

Repeated Crystallizations of Crude Pentamycin from Methanol

Figure 11:
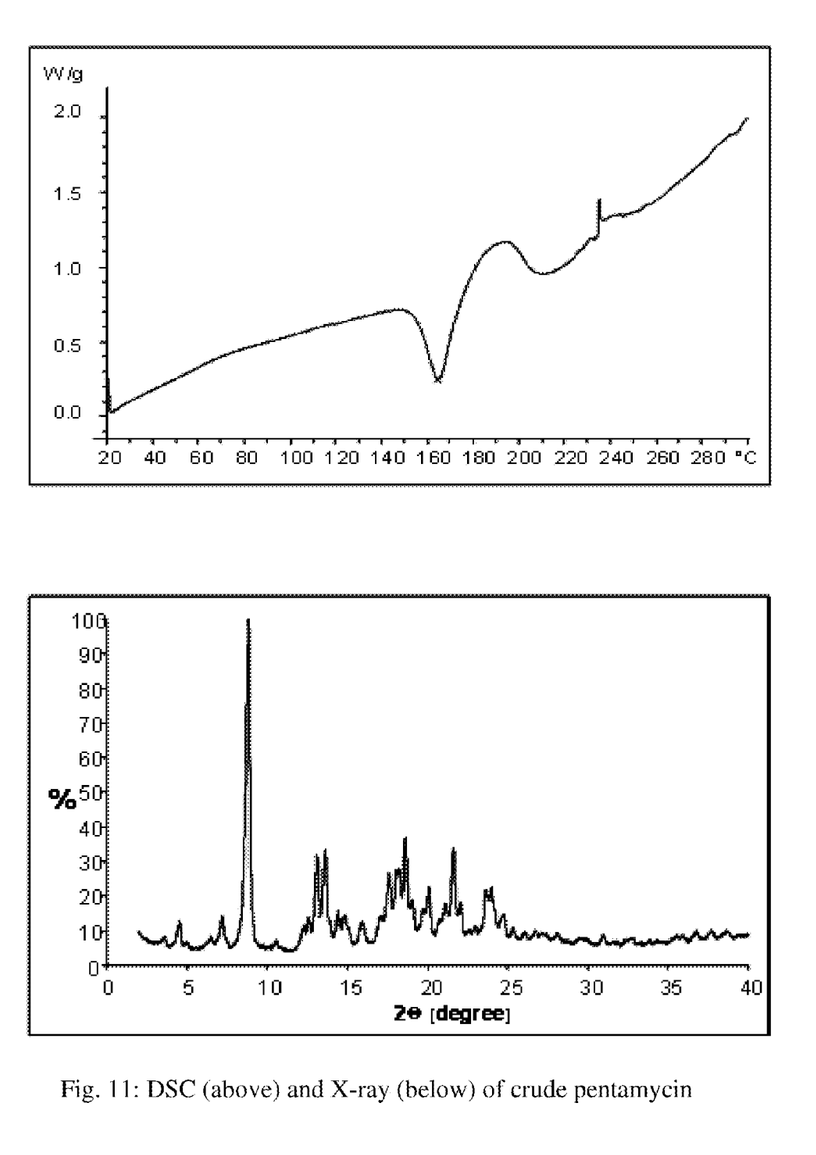
FIG. 11 shows a powder X-ray diffraction diagram (above) and DSC of crude pentamycin.
Figure 12:
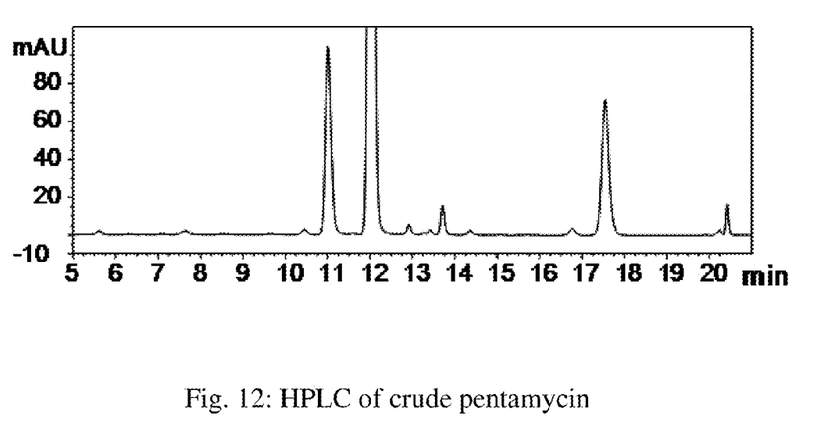
FIG. 12 shows a high pressure liquid chromatogram (HPLC) of crude pentamycin.

Crude pentamycin having the X-ray, DSC, and HPLC depicted in FIG. 11 and FIG. 12 respectively is crystallized three times from methanol as described in J. Antibiotics, ser. A, vol. XI, no. 1, January 1958, pp. 26-29:

10 g of crude pentamycin are stirred in 600 ml of boiling methanol for about 15 minutes. The hot methanol solution is filtered and the filtrate is heated again to reduce the volume of methanol until precipitation occurs. After cooling at room temperature and storage for 30 minutes the solid material is isolated by filtration and washed with 30 ml of cold (4° C.) methanol. The filter cake is dried by vacuum evaporation 30 minutes after reaching 16 mbar at 40° water bath temperature. The recovery is not investigated.

Two of three parts from the first methanol crystallization are resolved in 400 ml of boiling methanol. The clear solution is further heated under stirring to reduce the volume of methanol up to 150 ml. After cooling at room temperature and storage for 30 minutes the solid material is isolated by filtration and washed with 30 ml of cold methanol (4° C.). The filter cake is dried by vacuum evaporation 30 minutes after reaching 16 mbar at 40° water bath temperature. The recovery is not investigated.

Two of three parts from the second methanol crystallization are resolved in 300 ml of boiling methanol. The clear solution is further heated to reduce the volume of methanol up to approximately 75 ml. After cooling at room temperature and storage for 30 minutes the solid material is isolated by filtration and washed with 30 ml of cold methanol (4° C.). The filter cake is dried by vacuum evaporation 30 minutes after reaching 16 mbar at 40° C. water bath temperature. The recovery is not investigated.

Figure 13:
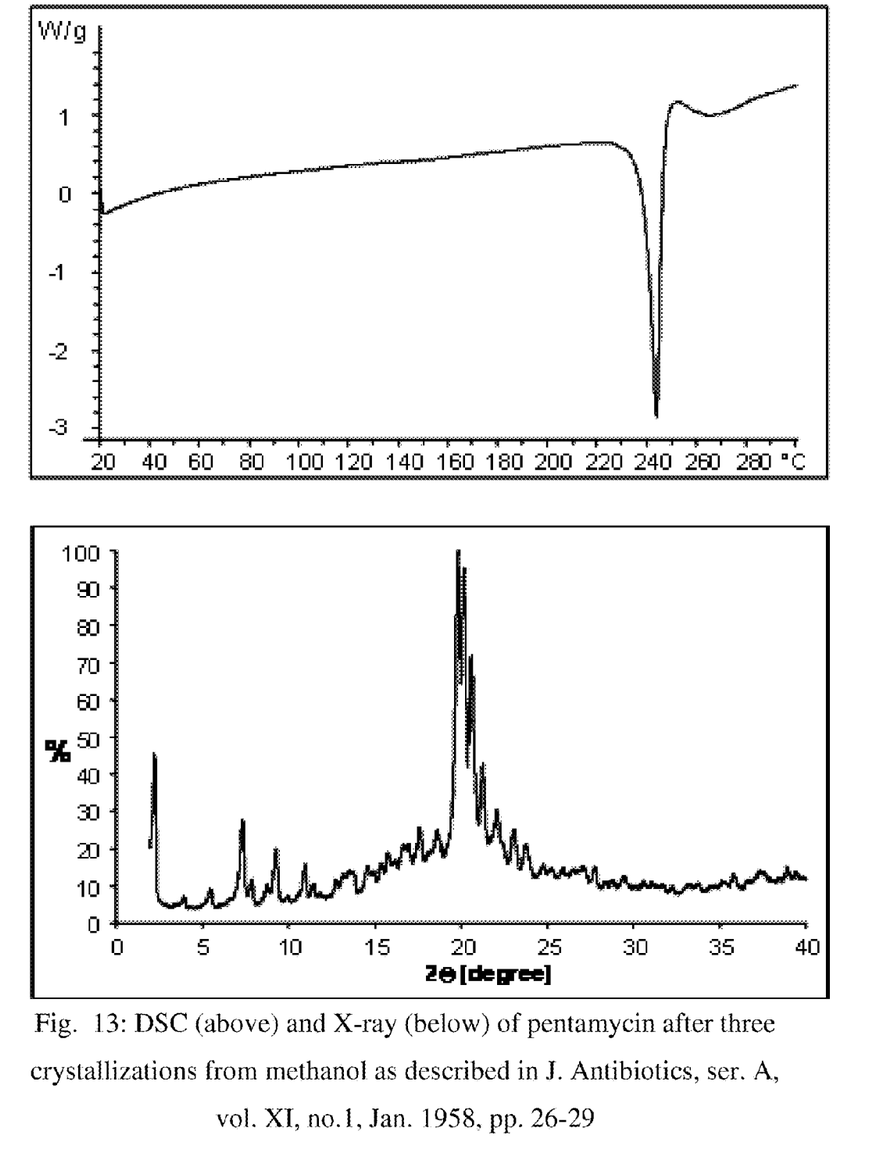
FIG. 13 shows a DSC (above) and powder X-ray diffraction diagram (below) of pentamycin recorded after three crystallizations from methanol as described in J. Antibiotics, ser. A, vol. XI, no.1, January 1958, pp. 26-29.
Figure 14:
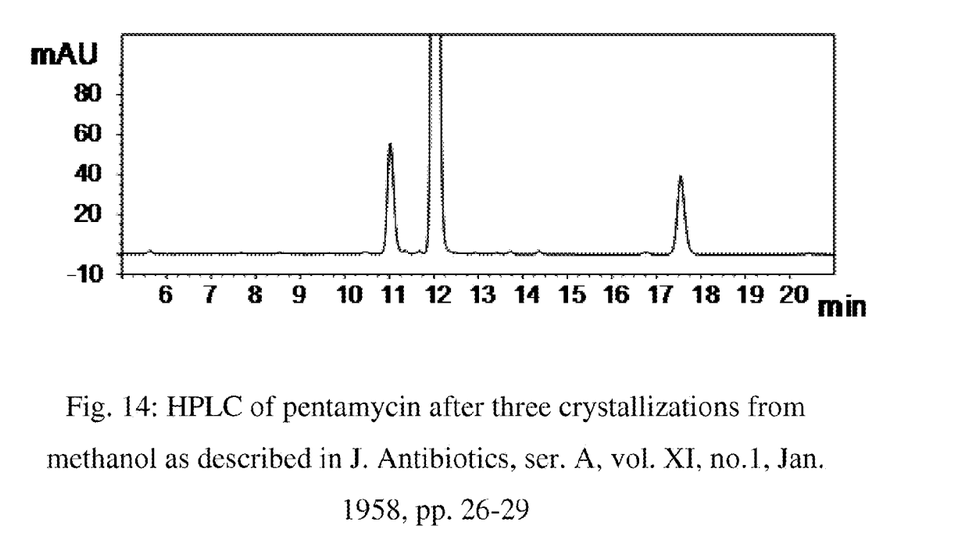
FIG. 14 shows a HPLC of pentamycin recorded after three crystallizations from methanol as described in J. Antibiotics, ser. A, vol. XI, no. 1, January 1958, pp. 26-29.

The obtained product is pentamycin in a chemical purity of about 90% only as evident from its HPLC chromatogram depicted in FIG. 14. A comparison of FIG. 14 (HPLC after 3 crystallizations) with FIG. 12 (HPLC before the crystallizations) shows that some minor impurities have been removed, but the two major impurities are still there. The powder x-ray diffraction spectrum and the DSC (peak at 243.55° C.) of the obtained product are depicted in FIG. 13. The DSC peak at 243.55° C. compares to the melting point (decomposition) of 236-237° C. reported in J. Antibiotics, ser. A, vol. XI, no. 1, January 1958, pp. 26-29 and is clearly lower than the peak of 254.42° C. shown in FIG. 7 for polymorph A of pentamycin according to the present invention.

Example 9

Stability of Polymorph A of Pentamycin

The stability of more than 95% pure polymorph A on exposure to air and heat is compared to the stability of amorphous pentamycin (containing more than 95% pure pentamycin) as follows:

Amorphous pentamycin is prepared by precipitation from a solution of more than 95% pure pentamycin in dimethylsulfoxide by adding acetonitrile, followed by filtering and drying the precipitate.

More than 95% pure polymorph A of pentamycin is prepared by crystallization from a solution of more than 95% pure pentamycin in dimethylsulfoxide by adding ethyl acetate, followed by filtering and drying the precipitate.

A sample of the thus obtained amorphous pentamycin and a sample of the thus obtained polymorph A are incubated in an open vessel about six days at 60° C. and additionally 2 weeks at 40° C. The process of degradation is monitored by HPLC, measuring the decrease of the purity relative to the inital state at zero time (t0) set on 100%. After the incubation the amount of degradation of amorphous pentamycin is 11% whereas the amount of degradation of polymorph A is only 1%.

Example 10

Reworking Example 1 of British Patent No. 884,711

Analogously as described in Example 1 on page 8 of British patent no. 884,711, 3.5 kg of fermentation broth cuttings are extracted with 16 litres of butanol, the extract is concentrated under vacuum at 55° C. to 600 ml, and then 600 ml of distilled water are added. After concentration to a paste, it is washed with 1 litre of diethyl ether and filtered. 40 g of the obtained solid are further processed by extraction with methanol in a soxhlet during 6 hours, crystallized at 4° C., and filtered. According to HPLC, the obtained crystals contain 67.3% pure pentamycin. This compares to a purity of approximately 75% reported on page 8, lines 33 and 35, of the British patent. 1.9 g of the crystals are washed in a soxhlet with 100 ml of chloroform during 2 hours) and then extracted in a soxhlet for 2 hours with diethyl ether. The obtained solid is re-extracted in a soxhlet with methanol during 4 hours. The crystals obtained by cooling to 4° C. during 40 hours and drying under vacuum contain according to HPLC 70.1% pure pentamycin. This compares to page 8, line 41 of British patent 884,711, according to which allegedly "pure" lagosin (pentamycin) is obtained.

The invention claimed is:

1. Pentamycin in the form of polymorph A with a chemical purity exceeding 96%, characterized by the following 2theta values, ±about 0.2°, of the most intense lines in the X-ray powder diffraction spectrum, the relative intensities being provided as rough indication only:

| 2Theta angle | Relative intensity | 2Theta angle | Relative intensity | 2Theta angle | Relative intensity | 2Theta angle | Relative intensity |
|---|---|---|---|---|---|---|---|
| 2.22 | 100 | 7.29 | 33 | 9.25 | 15 | 19.78 | 51 |
| 20.17 | 52 | 20.62 | 25 | 21.24 | 17 | | |

2. Pentamycin in the form of a flake-shaped morpholine solvate with a purity exceeding 96%.

3. A method for significantly decreasing the rate of degradation of pentamycin with a purity exceeding 96% comprising the step of transforming pentamycin with a purity exceeding 96% into its polymorph A.

4. The method according to claim 3 wherein the transformation into polymorph A is effected by crystallization from a solution of more than 96% pure pentamycin in dimethylsulfoxide after adding ethyl acetate.

* * * * *